United States Patent [19]

Kaiser et al.

[11] 4,347,190
[45] Aug. 31, 1982

[54] 2-METHYL-2-VINYL-5-(1'-HYDROXY OR ACYLOXY-1',5'-DIMETHYL-HEX-4'-EN-1'-YL)TETRAHYDROFURAN

[75] Inventors: Roman Kaiser, Clifton, N.J.; Dietmar Lamparsky, Wangen, Switzerland

[73] Assignee: Givaudan Corporation, Clifton, N.J.

[21] Appl. No.: 187,937

[22] Filed: Sep. 12, 1980

Related U.S. Application Data

[62] Division of Ser. No. 71,160, Aug. 30, 1979, Pat. No. 4,255,337.

[30] Foreign Application Priority Data

Sep. 8, 1978 [CH] Switzerland ............... 9470/78

[51] Int. Cl.³ ............... C07D 307/17; C07D 307/16
[52] U.S. Cl. ............................... 549/497; 549/499
[58] Field of Search ................... 260/347.4, 347.8

[56] References Cited

U.S. PATENT DOCUMENTS 3,892,782  7/1975  Buchi ..................... 260/346.11

FOREIGN PATENT DOCUMENTS 2452083  5/1975  Fed. Rep. of Germany.
48-61468  8/1973  Japan.

OTHER PUBLICATIONS

Gildemeister et al., Die Atherischen Ole, vol. III d (1966) pp. 732–734.
Stoll et al., Helv. Chim. Acta, vol. 50 (1967) p. 628.
Sipina, Recueil, vol. 87 (1968) p. 715.
Thomas et al., Helv. Chim. Acta, vol. 54 (1971) p. 1890.
Thomas, Helv. Chim. Acta, vol. 57 (1974) p. 2081.
Thomas et al., Helv. Chim. Acta, vol. 57 (1974) pp. 2062, 2066, 2076.
Kaiser et al., Helv. Chim. Acta, vol. 62 (1979) p. 1887.

*Primary Examiner*—Richard Raymond
*Attorney, Agent, or Firm*—Robert F. Tavares

[57] ABSTRACT

The invention is concerned with odorant and/or flavoring substances, intermediates therefor, a process for the manufacture of said substances, odorant and/or flavoring compositions containing same and a process for the preparation of said compositions. The invention is also concerned with a method of imparting an odor and/or a flavor to materials using said substances or compositions.

3 Claims, No Drawings

2-METHYL-2-VINYL-5-(1'-HYDROXY OR ACYLOXY-1',5'-DIMETHYL-HEX-4'-EN-1'-YL)TETRAHYDROFURAN

This is a division of application Ser. No. 71,160, filed Aug. 30, 1979, now U.S. Pat. No. 4,255,337.

The novel odorant and/or flavoring substances provided by the present invention are compounds of the formula

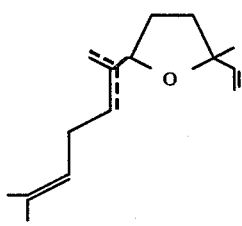

I wherein one of the dotted lines represents an additional bond.

FIELD OF THE INVENTION

This invention relates to the field of fragrances and flavorants.

SUMMARY OF THE INVENTION

As aforesaid, the novel odorant and/or flavoring substances provided by the present invention are compounds of the formula

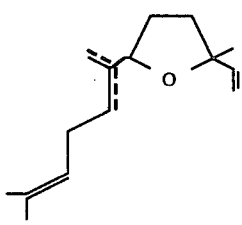

I wherein one of the dotted lines represents an additional bond.

Formula I is intended to embrace on the one hand all 4 isomers of 2-methyl-2-vinyl-5-(1'-methylene-5'-methyl-hex-4'-en-1'-yl)-tetrahydrofuran, i.e. all 4 enantiomers of the two diastereoisomeric forms Ia and Ib:

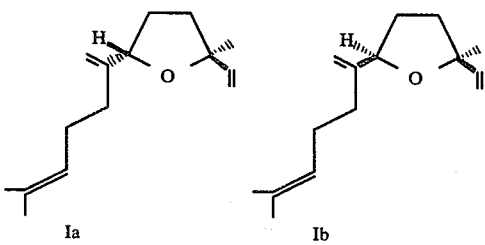

On the other hand, formula I hereinbefore is intended to embrace all 8 stereoisomers of 2-methyl-2-vinyl-5-(1',5'-dimethyl-hexa-1',4'-dien-1'-yl)-tetrahydrofuran, i.e. the 8 enantiomers of the 4 diastereoisomeric forms Ic to If:

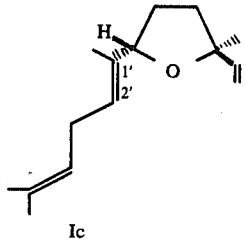 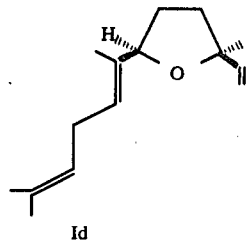

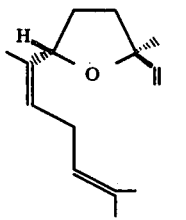 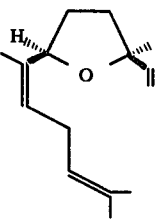

side chain to vinyl group:

|  | trans | cis | trans | cis |
|---|---|---|---|---|
| $C_{1'} = C_{2'}$: | trans | trans | cis | cis |

The present invention is also concerned with a process for the manufacture of the compounds of formula I.

This process comprises dehydrating or deacylating 2-methyl-2-vinyl-5-[1'-(hydroxy or acyloxy)]-1',5'-dimethyl-hex-4'-en-1'-yl)-tetrahydrofuran, such process leading to the mixtures Ia–If and Ia–Id respectively In the process provided by the present invention the hydroxyl or acyloxy oxygen function is removed in the form of a β-elimination reaction.

As the starting material in the present process there can be used, for example, the isomer mixture II or the individual isomers IIa–IId of 2-methyl-2-vinyl-5-(1'-hydroxy-1',5'-dimethyl-hex-4'-en-1'-yl)-tetrahydrofuran:

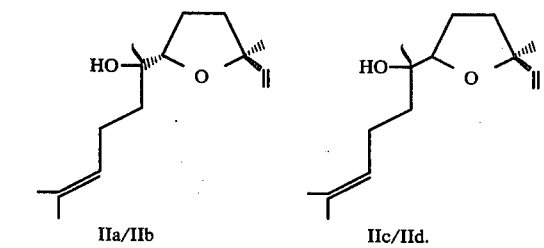

These individual isomers of II or the isomer mixture can be dehydrated directly to give I using suitable reagents.

Suitable dehydrating reagents are, for example, phosphorus oxyhalides such as phosphorus oxychloride in the presence of an excess of a base, such as pyridine, thionyl chloride, in the presence of an excess of a base, such as pyridine, organic and inorganic acids such as p-toluenesulphonic acid, oxalic acid, hydrochloric acid etc, acid salts such as potassium bisulphate etc.

In this manner I is obtained in the form of the isomer mixture of Ia–If or, when the diastereomer pairs IIa/IIb are used as the starting material, in the form of the mixture Ia, Ic and Ie or, when the diastereomer pairs IIc/IId are used as the starting material, in the form of the mixture Ib, Id and If. Ie or If are present in the respective mixtures of products in only slight amounts, but their presence clearly shows up from the column-chromatographical and gas-chromatographical working-up of the mixture on the basis of the gas-chromatographical analysis (shoulder in the case of Ia or Ib on packed columns or separated peaks on glass capillary columns), and the appearance of characteristic signals associated therewith in the NMR-spectrum of the isolated samples of Ia or Ib.

However, II is preferably firstly converted into an acid ester (e.g. the acetate, propionate, butyrate or benzoate) and then the esters IIIa–IIId corresponding to the alcohols II or their mixtures are deacylated, conveniently by subjecting them to pyrolysis.

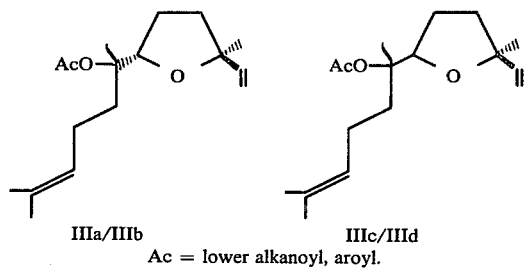

IIIa/IIIb    IIIc/IIId
Ac = lower alkanoyl, aroyl.

The esterification can be carried out according to methods known per se; for example by treating II with a reactive acid derivative of AcOH such as a halide or the anhydride. In this case, the esterification is carried out in the presence of a base such as dimethylaniline, diethylaniline, pyridine etc. III is then pyrolysed to give I.

The pyrolysis of III can be carried out, for example, by simply heating the individual esters or the ester mixture in a Hickmann flask under a nitrogen atmosphere; for example, to 260°–300° C. The resulting acidic distillate can be taken up in a solvent (e.g. an ether), washed neutral with bicarbonate solution and water, dried and concentrated. Improved results are obtained when the material to be pyrolysed is added dropwise as a ca 20–40% (e.g. 30%) solution in hexane, benzene etc to a pyrolysis tube which is conditioned at a temperature between ca 300°–500° C., especially 370°–430° C., and which is conveniently loaded with glass Raschig rings. However, other carrier materials such as ceramic filling substances, fine iron or copper gauze etc can also be used.

The compounds of formulae II and III are novel and also form part of the present invention.

As the starting materials for the preparation of II there can be used the trans-and cis-2-methyl-2-vinyl-5-acetyl-tetrahydrofurans IVa and IVb which are known from the literature [see A. F. Thomas, R. Dubini, Helv. 57, 2066 [1974]].

The Grignard reaction of, for example, 4-methyl-3-penten-1-yl-magnesium bromide [F. Medina, A., Manjarrez, Tetrah. 20, 1807 [1964]] with IVa or IVb or with the 2:1 mixture of IVa/IVb normally occurring in the synthesis of IV leads to the diastereoisomer mixture of the 2-methyl-2-vinyl-5-(1'-hydroxy-1',5'-dimethyl-hex-4'-en-1'-yl)-tetrahydrofurans IIa/IIb or IIc/IId in the ratio of in each case 9:1, or to the mixture of IIa, IIb, IIc, IId in the ratio of 18:2:9:1.

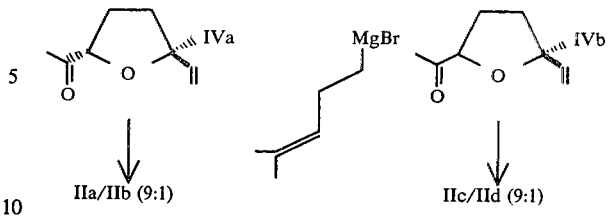

IIa/IIb (9:1)    IIc/IId (9:1)

The separation of the isomer mixture (of I, II and III or IV), can be carried out in the usual manner; for example, by column chromatography or preparative gas chromatography. As will be evident from the following, the isomers of I do not differ fundamentally in their organoleptic properties, so that on economical grounds especially the isomer mixture can be used.

The compounds of formula I have particular organoleptic properties, on the basis of which they are excellently suited as odorant and/or flavouring substances.

The invention is accordingly also concerned with the use of compounds of formula I, especially in practically pure form or in the form of mixtures (with the exception of natural mixtures containing a compound of formula I) as odorant and/or flavouring substances.

The expression "practically pure" is used herein to mean, in particular, a compound of formula I which is free from accompanying substances which are present besides compounds of formula I in natural extracts. As practically pure compounds of formula I in the scope of the present invention there should be understood, in particular, synthetically manufactured compounds of formula I.

The natural mixtures containing compounds of formula Ic and Id should therefore be excluded, since in the course of the present work it has been found that Ic/Id in the ratio of ca 1:1 are present to an extent of less than 0.01% in the absolute oil of Osmanthus fragrans Lour.

The compounds of formula I possess a fresh, fruity, very natural odour which is also reminiscent in certain respects of apples, pears and young plant buds. The individual isomers possess an almost similar odour, except that an additional terpene-like note can be identified in the case of the isomers Ia and Ib. On economical grounds, the isomer mixture is therefore advantageously used. The compounds can therefore be used, for example, for the perfuming or flavouring of products such as cosmetics (soaps, salves, powders, toothpastes, mouth washes, deodorants, shampoos, lotions etc.), detergents, foodstuffs, luxury consumables and drinks, the compounds preferably not being used alone but in the form of compositions with other odorant or flavouring substances. Such odorant or flavouring compositions containing compounds of formula I also form part of the present invention.

The odorant and flavouring compositions provided by this invention are produced in a manner known per se (addition of compounds of formula I to known odorant or flavouring compositions or admixture of compounds of formula I with natural or synthetic compounds or mixtures suitable as the ingredients of odorant or flavouring compositions).

On the basis of their aforementioned original notes, the compounds of formula I are suitable as odorants, especially in combination with a series of natural and synthetic odorant substances such as, for example:

Galbanum oil, mastix oil, vetiver oil, patchouli oil, sandalwood oil, mandarin oil, petitgrain oil, ylang-ylang oil, basil oil, tree moss absolute, patchouli leaf oil, cedar oil, pine oil, laurel oil, cotus root oil, calamus oil, mugwort oil, camomile oil, wormwood oil, wormseed oil, celery seed oil, angelica seed oil, star anis oil, thyme oil, rosemary oil, lavender oil, lavandin oil, aspic oil, sage oil, neroli oil, bergamotte oil, lemon oil, orange oil, grapefruit oil, geranium oil, benzoin resinoid, melilotus absolute, jasmine absolute, rose oil, cananga oil, coriander oil, cassia absolute, narcissus absolute, verbena absolute or oil, violet leaf absolute, tuberose absolute etc; aldehydes such as hydroxycitronellal, cyclamen aldehyde, benzaldehyde, p-tert.butyl-α-methylhydrocinnamaldehyde, α-hexylcinnamaldehyde, 3,5-dimethyl-cyclohex-3-en-1-yl-carboxaldehyde, citral, citronellal, 2,6-dimethyl-5-hepten-1-al, isovaleraldehyde, trans-2-hexenal, sorbic aldehyde, trans-2-octenal, n-octanal, n-nonanal, trans-2-cis-6-nonadienal, 2,4-decadienal, methylnonylacetaldehyde etc;

ketones such as α-ionone, β-ionone, allylionone, acetanisole, 4-(p-hydroxyphenyl)-2-butanone, camphor, methone, carvone, pulegone etc;

acetals and ketals such as phenylacetaldehyde dimethyl acetal, phenylacetaldehyde glycerine acetal, 2-methyl-1,3-dioxolan-2-ethyl acetate, capronaldehyde dimethyl acetal etc;

ethers such as eugenol methyl ether, methyl 1-methyl-cyclododecyl ether, anethol, estragol etc;

phenolic compounds such as vanillin, eugenol, isoeugenol, creosol etc;

alcohols such as butanol, n-hexanol, cis-3-hexenol, trans-2,cis-6-nonadienol, cis-6-nonenol, linalool, geraniol, nerol, citronellol, nerolidol, farnesol, benzyl alcohol, phenylethyl alcohol, cinnamic alcohol etc;

esters such as methyl dihydrojasmonate, linalyl acetate, bornyl acetate, geranyl propionate, cedryl acetate, vetiveryl acetate, ethyl acetate, isoamyl acetate, ethyl butyrate, p-tert.butyl-cyclohexyl acetate, o-tert.butylcyclohexyl acetate, Myraldyl acetate ® (Givaudan), benzyl acetate, benzyl salicylate, styrallyl acetate, ethyl α-methylphenyl-glycidate, piperonyl acetate, maltyl isobutyrate, dimethylbenzylcarbinyl butyrate, cis-3-hexenyl acetate, cis-3-hexenyl salicylate, ethyl 2,4-decadienoate, ethyl acetoacetate, etc;

lactones such as γ-undecalactone, γ-decalactone, γ-nonalactone, δ-decalactone, δ-octalactone, coumarin etc;

acids such as lactic acid, butyric acid, α-methylbutyric acid, trans-2-hexenoic acid, trans-2-octenoic acid etc;

compounds having a musk-like and amber-like odour such as ethylene brassylate, 4-acetyl-6-tert.butyl-1,1-dimethylindane, 12-oxahexadecanolide, 8α,12-oxido-13,14,15,16-tetranorlabdane etc;

sulphur-containing compounds such as p-menthane-8-thiol-3-one, dimethylsulphide and other sulphides and disulphides etc; and nitrogen-containing compounds such as methyl anthranilate, indole, isobutylquinoline, various pyrazines, 5-methyl-heptan-3-one-oxime etc.

As will be evident from the following Examples illustrating the use of the compounds of formula I, interesting effects can be achieved with said compounds. It is particularly outstanding that linalool/linalyl acetate mixtures are modified in an advantageous manner by compounds of formula I in that the resulting complexes are very natural and have an unexpected radiance. Since synthetic linalool and linalyl acetate are important and much-used compounds in perfumery and since these two compounds, moreover, are often the main components of essential oil, this fact is of considerable practical significance. The compounds of formula I can therefore be used with effect for the production of perfume compositions having a linalool/linalyl acetate odour or for the reconstitution of essential oils having a linalool/linalyl acetate odour such as, for example, the oils of the lavender, petitgrain, neroli, sage, bergamot group, etc.

Since the isomer mixture of formula I also enriches in a similar manner complexes between linalool and benzyl acetate (typical for jasmine and other flowery notes), linalool and methyl benzoate (typical for ylang-ylang direction), benzyl acetate and phenylethyl alcohol (typical for hyacinth compositions) and citronellol and phenylethyl alcohol (typical for rose direction) etc, it is well suited for the modification of flowery compositions or for the co-use in the reconstitution of flower essences or absolutes of the jasmine, rose, hyacinth, narcissus, ylang-ylang and like types.

In the production of such compositions, the aforementioned known odorants can be used according to methods which are known to the perfumer; for example, as described by W. A. Poucher, Perfumes, Cosmetics and Soaps, Vol. 2, 7th Edition, Chapman and Hall, London, 1974.

The concentration in which the compounds of formula I are used can vary within wide limits depending on the purpose of use; for example, between about 0.01 wt. % in the case of detergents and about 30 wt. % in the case of alcoholic solutions. In perfume bases or concentrates the concentrations can, of course, also be higher. The perfume bases can be used in the customary manner for the perfuming of Eau de Cologne, eau de toilette, lotions, creams, shampoos, soaps, detergents etc.

As flavouring substances, the compounds of formula I can be used, for example, for the production or improvement, intensification, enhancement or modification of fruit or berry flavours in foodstuffs (yoghurt, sweet goods, etc.), in luxury consumables (tea etc.) and in drinks (lemonades etc).

The pronounced flavour qualities of especially practically pure, particularly of synthetically manufactured, compounds of formula I enable them to be used in low concentrations. A suitable range is, for example, 0.05 ppm–100 ppm, preferably 0.1 ppm–20 ppm, in the finished product (i.e. the flavoured foodstuff, luxury consumable or drink).

In the following Table there are compiled some effects which can be achieved with the compounds of formula I.

TABLE

| Flavour | Concentration | Effect |
|---|---|---|
| Apple | ppm in the finished product 0.05–100 ppm, especially 0.1–10 ppm | improved |
| Pear | ppm in the finished product 0.05–100 ppm, especially 0.1–10 ppm | improved |

| Flavour | Concentration | Effect |
|---|---|---|
| Apricot, peach, blueberry, gooseberry | ppm in the finished product 0.05–100 ppm, especially 0.1–10 ppm | enriches the flavour by producing an aspect reminiscent of the fruit skin |

The compounds of formula I can be mixed with the ingredients used for flavouring compositions or added to such flavourants in the customary manner. Among the flavourants which can be used in accordance with the present invention there are to be understood flavouring compositions which can be diluted or dispersed in edible materials in a manner known per se. The present flavouring compositions can be converted according to methods known per se into the customary forms of use such as solutions, pastes or powders. They can be spray-dried, vacuum dried or lyophilised.

The known flavouring substances conveniently used in the production of the flavouring compositions provided by this invention are either referred to hereinbefore or can readily be obtained from the literature such as, for example, from J Merory, Food Flavorings, Composition, Manufacture and Use, Second Edition, The Avi Publishing Company Inc., Westport, Conn. 1968, or G. Fenaroli, Fenaroli's Handbook of Flavor Ingredients, Second Edition, Volume 2, CRC Press, Inc., Cleveland, Ohio, 1975.

For the production of such customary forms of use there can be used, for example, the following carrier materials, thickening agents, flavour-improvers, spices, auxiliary ingredients etc.:

Gum arabic, tragacanth, salts or brewers' yeast, alginates, carrageen or similar absorbents; indoles, maltol, spice oleoresins, smoke flavours; cloves, sodium citrate, monosodium glutamate, disodium inosine-5'-monophosphate (IMP), disodium guanosine-5-phosphate (GMP); or special flavouring substances, water, ethanol, propyleneglycol or glycerine.

The following Examples illustrate the present invention:

EXAMPLE 1

2-Methyl-2-vinyl-5-(1'-hydroxy-1',5'-dimethyl-hex-4-en-1'-yl)-tetrahydrofurans IIa/IIb and IIc/IId A solution of 4.0 g (0.026 mol) of trans-2-methyl-2-vinyl-5-acetyltetrahydrofuran IVa in 10 ml of ether is dropped at 0° C. over a period of 20 minutes into a Grignard solution prepared from 5.08 g (0.031 mol) of 4-methyl-3-penten-1-yl bromide in 20 ml of ether and 0.76 g (0.031 mol) of magnesium shavings in 10 ml of diethyl ether. Subsequently, the mixture is stirred at reflux for 1 hour, then cooled and worked-up in the customary manner. There are obtained 4.2 g of crude product which contains the diastereoisomer pair IIa/IIb in the ratio of 9:1.

In an analogous manner, from 3.4 g (0.022 mol) of IVb there are obtained 4.1 g of crude product which contains the diastereoisomer pair IIc/IId in the ratio of 9:1. For characterization, IIa–IId are isolated in pure form by preparative gas chromatography.

In an analogous manner, from 98.0 g (0.64 mol) of the 2:1-mixture of the 2-methyl-2-vinyl-5-acetyl-tetrahydrofurans and 130.4 g (0.80 mol) of 4-methyl-3-penten-1-yl bromide there are obtained 120 g of crude product from which there can be obtained by distillation over a 20 cm Widmer column 100.2 g (66%) of the alcohol mixture IIa–IId in the ratio of 18:2:9:1. Boiling point 93° C./0.05 Torr.

Spectral data

IIa

IR: 3560, 3460 (internal H-bridge), 1640, 1180, 1150, 1120, 1090, 1050, 1020, 990, 918 cm$^{-1}$.

NMR: 1.10 (3H, s); 1.32 (3H, s); 1.64+1.70 (each 3H, s); 3.84 (1H, m); 4.9–5.3 (2H, AB-part); 5.75–6.05 (1H, X-part)~5.10 (1H, dxd) δ ppm.

MS: 238 (M$^+$, 1) 155 (7), 138 (28), 127 (12), 111 (27), 109 (100), 93 (30), 81 (16), 69 (88), 55 (28), 43 (74), 41 (45).

IIb

IR: 3560, 3460, 1640, 1180, 1125, 1095, 1050, 1025, 990, 918 cm$^{-1}$.

NMR: 1.22 (3H, s); 1.32 (3H, s); 1.64+1.70 (each 3H, s); 3.82 (1H, m); 4.9–5.3 (2H, AB-part); 5.75–6.05 (1H, X-part); ~5.10 (1H, dxd) δ ppm.

MS: as 2a.

IIc

IR: 3550, 3460, 1640, 1160, 1110, 1085, 1050, 1030, 1015, 990, 955, 915 cm$^{-1}$.

NMR: 1.10 (3H, s); 1.32 (3H, s); 1.64+1.70 (each 3H, s); 3.90 (1H, m); 4.9–5.3 (2H, AB-part); 5.84–6.14 (1H, X-part); ~5.10 (1H, dxd) δ ppm.

MS: 238 (M$^+$, 1), 155 (5), 138 (23), 127 (13), 111 (24), 109 (100), 93 (28), 81 (15), 69 (85), 55 (26), 43 (70), 41 (42).

IId

IR: 3560, 3460, 1640, 1180, 1110, 1055, 1025, 990, 915 cm$^{-1}$.

NMR: 1.24 (3H, s); 1.32 (3H, s); 1.62+1.68 (each 3H, s); 3.88 (1H, m); 4.9–5.3 (2H, AB-part); 5.83–6.12 (1H, X-part); ~5.10 (1H, dxd) δ ppm.

MS: as 2c.

2-Methyl-2-vinyl-5-(1'-acetoxy-1',5'-dimethyl-hex-4'-en-1'-yl)-tetrahydrofurans IIIa–IIId 40.0 g (0.168 mol) of the alcohol mixture IIa–IId are dissolved in 70 ml of dimethylaniline, treated with a mixture of 13.2 g (0.168 mol) of acetyl chloride and 8.6 g (0.084 mol) of acetic acid anhydride and subsequently stirred at 60° C. for 15 hours. The cooled mixture is taken up in diethyl ether, washed successively with water, dilute hydrochloric acid, soda solution and again with water, dried and concentrated. There are obtained 46.5 g of acetate mixture IIIa–IIId which are subsequently subjected to pyrolysis.

In an analogous manner, in each case 3.0 g of the diastereoisomer mixture IIa/IIb or IIc/IId are converted into the acetate mixture IIIa/IIIb (9:1) or IIIc/IId (9:1) and the crude products obtained are purified by preparative gas chromatography.

Spectral data

IIIa/IIIb

IR: 1738, 1250, 1175, 1130, 1060, 1020, 942, 920, (9:1) 835 cm$^{-1}$.

NMR 1.30 (3H, s); 1.40 (3H, s); 1.60+1.69 (each 3H, s); 2.00 (3H, s); 4.31 (1H, m); 4.9–5.3 (2H, AB-part of the vinyl group); 5.65–6.12 (1H, X-part of the vinyl group); ~5.10 (1H, m) δ ppm.

MS: 280 (M$^+$, 1), 151 (67), 138 (100), 111 (98), 109 (90), 96 (30), 93 (51), 81 (30), 69 (50), 55 (21), 43 (85), 41 (37).

IIIc/IIId

IR: 1738, 1250, 1175, 1062, 1020, 980, 920, 835 (9:1) cm$^{-1}$.

NMR: 1.30 (3H, s); 1.42 (3H, s); 1.59+1.67 (each 3H, s); 1.98 (3H, s); 4.32 (1H, m); 4.8-5.3 (2H, AB-part); 5.6-6.2 (1H, X-part); ~5.10 (1H, M).

MS: 280 (M$^+$, 1); 151 (62), 138 (96), 111 (100), 109 (95), 96 (32), 93 (54), 81 (32), 69 (53), 43 (95), 41 (42).

2-Methyl-2-vinyl-5-(1'-methylene-5'-methyl-hex-4'-en-1'-yl)-tetrahydrofurans+2-methyl-2-vinyl-5-(1',5'-dimethyl-hexa-1',4'-dien-1'-yl)-tetrahydrofurans Ia-Id The pyrolysis apparatus used is a quartz tube of 50 cm length and 5 cm diameter which is filled with glass Raschig rings of 2-4 mm diameter and conditioned at a temperature of 400° C.±5° C. with a heating mantle. 46.5 g (0.165 mol) of the acetate mixture IIIa-IIId are dissolved in 120 ml of hexane and dropped into the pyrolysis tube over a period of 2 hours while simultaneously passing through a nitrogen stream at a rate of 0.3 liters/minute. The pyrolysis product which issues is condensed in a cooled vessel, washed with sodium bicarbonate solution, dried and concentrated. There are obtained 19.0 g of crude product which contains Ia, Ib, Ic and Id in the ratio of about 4:2:2:1 (gas-chromatographical detection). Distillation of the crude product over a 20 cm Widmer column yields 14.5 g of an olfactorily good mixture of Ia-Id of boiling point 78°-80° C./0.05 mmHg.

In an analogous manner, in each case 2.5 g of the diastereoisomer mixture IIIa/IIIb or IIIc/IIId are pyrolysed to give Ia+Ic (2:1) or Ib+Id (2:1).

Spectral data

Ia

IR: 3080, 1645, 1235, 1125, 1095, 1050, 1020, 988, 916, 892, 820 cm$^{-1}$.

NMR: 1.36 (3H, s), 1.62+1.70 (each 3H, s), 4.40 (1H, m), 4.82+5.10 (each 1H), ~5.1 (1H, m), 4.9-5.3 (2H, AB-part of the vinyl group), 5.75-6.05 (1H, X-part of the vinyl group) δ ppm.

MS: 220 (M$^+$, 6), 152 (37), 137 (39), 119 (32), 109 (94), 93 (52), 81 (46), 69 (100), 67 (62), 55 (37), 41 (87), further characteristic fragments at m/e 135 (25), 107 (47), 95 (50), 68 (37), 43 (35).

Ib

IR: 3080, 1645, 1245, 1122, 1095, 1050, 1020, 988, 915, 894 cm$^{-1}$.

NMR: 1.34 (3H, s), 1.64+1.70 (each 3H, s), 4.44 (1H, m), 4.84+5.14 (each 1H), ~5.1 (1H, m), 4.9-5.3 (2H, AB-part), 5.83-6.12 (1H, X-part), δ ppm.

MS: 220 (M$^+$, 2), 152 (25), 137 (27), 119 (20), 109 (52), 93 (31), 81 (29), 69 (66), 67 (47), 55 (41), 41 (100), further characteristic fragments at m/e 135 (20), 107 (27), 95 (26), 68 (24), 43 (35).

Ic

IR: 1642, 1123, 1098, 1018, 992, 920, 875 cm$^{-1}$.

NMR: 1.34 (3H, s), 1.64 (6H, 2s), 1.68 (3H, s), 1.80 (2H, m), 1.88 (2H, m), 2.72 (2H, dxd, J~6.8 Hz), 4.32 (1H, m), 4.9-5.3 (2H, AB-part), 5.7-6.0 (1H, X-part), 5.10 (1H, dxd, 5.43 (1H, dxd, J~6.8 Hz) δ ppm.

MS: 205 (M$^+$—CH$_3$, 1), 151 (100), 135 (9), 123 (11), 109 (27), 95 (32), 93 (25), 81 (27), 69 (53), 67 (52), 55 (23), 41 (36), further characteristic fragments at m/e 82 (19), 67 (32), 53 (12), 43 (17).

Id

IR: 1642, 1122, 1098, 1058, 1022, 992, 920, 875 cm$^{-1}$.

NMR: 1.32 (3H, s), 1.64 (6H, 2s), 1.68 (3H, s), 1.7-2.1 (4H), 2.72 (2H, dxd J~7 Hz), 4.36 (1H, m), 4.9-5.3 (2H, AB-part), 5.8-6.1 (1H, X-part), ~5.10 (1H, dxd), 5.46 (1H, dxd, J~7 Hz) δ ppm.

MS: 205 (M$^+$—CH$_3$, 1), 151 (100), 135 (10), 123 (12), 109 (36), 95 (46), 93 (36), 81 (48), 69 (96), 67 (86), 55 (54), 41 (78) further characteristic fragments at m/e 82 (29), 67 (65), 53 (24), 43 (40).

EXAMPLE 1a

2-Methyl-2-vinyl-5-(1'-methylene-5'-methyl-hex-4'-en--1'-yl-tetrahydrofuran and 2-methyl-2-vinyl-5-(1',5'--dimethyl-hexa-1',4'-dien-1'-yl)-tetrahydrofurans Ia-If 2.4 ml of phosphorus oxychloride in 8 ml of pyridine are added dropwise to a solution, cooled to −10° C., of 0.80 g (3.4 mmol) of the diastereoisomer mixture IIa/IIb in 80 ml of pyridine so that a temperature of −5° C. is not exceeded. Subsequently, the mixture is stirred at −10° C. for 4 hours and then at room temperature for 20 hours, diluted with 200 ml of hexane, washed with water, dilute hydrochloric acid, sodium bicarbonate solution and again with water, dried and concentrated. There are obtained 0.63 g of crude product which contains Ia and Ic in the approximate ratio of 3:2. By column-chromatographical separation on a 40-fold amount of silica gel there are obtained with hexane/ether (30:1) fractions which are considerably enriched in Ia (0.25 g) and Ic (0.14 g). For characterisation, samples which are further purified by preparative gas chromatography (Carbowax 20 M) are used. Ia and Ic have the same spectral data as the compounds obtained according to Example 1. The NMR spectrum of Ia shows, however, at 2.74 ppm an additional weak signal ( ~10%) in the form of a dxd (J~7 Hz), although the sample is completely free from Ic. Ia is thus still contaminated with about 10% of Ie. Ie can be separated from Ia on a capillary column (50 m UCON). The mass spectrum of Ie taken via a GC-MS-coupling is almost identical with that of Ic.

In an analogous manner, 0.80 g of the diastereoisomer pair IIc/IId is dehydrated. After purification of the crude product by column chromatography and preparative gas chromatography, there are obtained Ib and Id which have the same spectral data as the compounds obtained according to Example 1. Here also, the NMR spectrum of Ib shows a contamination (10%) which is the isomer If by virtue of the dxd at 2.74 ppm (J~7 Hz). The mass spectrum of If taken via a GC-MS-coupling is almost identical with that of Id.

In the same manner as described above, the previously not separated mixture of IIa-IId (as obtained from the 2:1-mixture of IVa/IVb) is dehydrated at low temperatures to give the mixture Ia-If thus also including the isomers Ie and If with cis-configuration of the double bond between C$_{1'}$ and C$_{2'}$.

In the following Examples "I" preferentially stands for the isomer mixture Ia-Id as obtained by pyrolysis of the acetates IIIa-IIId.

EXAMPLE 2

(a) Fruity complex

|  | Parts by weight |
|---|---|
| Linalyl acetate | 500 |
| Dimethylbenzylcarbinyl butyrate | 450 |

-continued

| | Parts by weight |
|---|---|
| | 950 |

After the addition of 50 parts of I, the complex is fresher, more fruity, more natural and a bergamotte oil note results.

(b) Flowery-fruity complex

| | Parts by weight |
|---|---|
| Linalyl acetate | 400 |
| Linalool | 400 |
| | 800 |

After the addition of 100 parts of I, the complex is sweeter, more spicy and a bergamotte oil effects also results.

(c) Flowery complex

| | Parts by weight |
|---|---|
| Phenylethyl alcohol | 400 |
| Benzyl acetate | 400 |
| | 800 |

After the addition of 100 parts of I, the complex, which previously was somewhat sharp, becomes a flowery, harmonic perfumery base with a slight rose-like character.

EXAMPLE 3

| Perfumery base in the direction of strawberry | |
|---|---|
| | Parts by weight |
| Linalyl acetate | 300 |
| Benzyl acetate | 200 |
| Linalool | 200 |
| Dimethylbenzylcarbinyl butyrate | 200 |
| Bornyl acetate | 20 |
| Fructone ® (2-methyl-1,3-dioxolan-2-ethyl acetate) | 10 |
| Maltyl isobutyrate | 10 |
| Corps Cassis ® Givaudan (p-menthane-8-thiol-3-one) | 10 |
| γ-Undecalactone | 10 |
| | 960 |

If there are added to this strawberry base 40 parts of I, then it is modified in the direction of wild strawberry. The resulting base is much more aromatic, fresher and more natural.

EXAMPLE 4

| Perfumery base having a fruity direction | |
|---|---|
| | Parts by weight |
| Ethyl 3-methyl-3-phenylglycidate | 100 |
| Ethyl acetoacetate | 30 |
| Maltyl isobutyrate | 30 |
| Dimethylbenzylcarbinyl butyrate | 20 |
| Benzyl acetate | 10 |
| Ethyl acetate (10% in propyleneglycol) | 6 |
| Lemon oil | 4 |
| | 200 |
| Propyleneglycol | 700 |

-continued

| Perfumery base having a fruity direction | |
|---|---|
| | Parts by weight |
| Total | 900 |

The addition of 100 parts of I to this base which has a fruity direction with a slight strawberry character produces a complete change in the direction of apple.

EXAMPLE 5

| Perfumery base in the direction of apple | |
|---|---|
| | Parts by weight |
| Ethyl 3-methyl-3-phenylglycidate | 100 |
| o-Tert.butyl-cyclohexyl acetate | 40 |
| Ethyl acetoacetate | 30 |
| Maltyl Isobutyrate | 30 |
| Dimethylbenzylcarbinyl butyrate | 20 |
| Benzyl acetate | 10 |
| Cyclal ® Givaudan (2,4-dimethyl-3-cyclohexene-1-carboxaldehyde (10% in propyleneglycol) | 10 |
| Ethyl acetate (10% in propyleneglycol) | 6 |
| Lemon oil | 4 |
| | 250 |
| Propyleneglycol | 730 |
| Total | 980 |

If there are added to the apple base (direction of boiled apple) 20 parts of I, then it is changed in the direction of fresh and natural apple. The original base is somewhat reminiscent of apple pulp, whereas the novel base restores the odour of the apple skin.

EXAMPLE 6

| Perfumery base having a generally flowery direction | |
|---|---|
| | Parts by weight |
| Methyl dihydrojasmonate | 200 |
| Linalool | 200 |
| Benzyl acetate | 200 |
| Hydroxycitronellal | 100 |
| α-Hexylcinnamic aldehyde | 100 |
| Citronellol | 60 |
| γ-Undecalactone (10% in propyleneglycol) | 40 |
| Hexenyl acetate (10% in propyleneglycol) | 20 |
| Ylang oil | 10 |
| Phenylethyl alcohol | 10 |
| Indole (10% in propyleneglycol) | 20 |
| | 960 |

If there are added to this generally flowery base 40 parts of I, then it is changed in a pleasant manner in the direction of ylang and jasmine. It is now fuller and rounder.

EXAMPLE 7

| Perfumery base in the direction of melon | |
|---|---|
| | Parts by weight |
| Myraldyl acetate$^R$ Givaudan | 120 |
| Dimethylbenzylcarbinyl butyrate | 120 |
| Cyclamen aldehyde | 80 |
| Hexenyl salicylate | 100 |
| Fructone ® 60 | |
| Melonal ® (2,6-dimethyl-5-hepten-1-al) (10% in propyleneglycol) | 60 |

| Perfumery base in the direction of melon | |
|---|---|
| | Parts by weight |
| Cis-6-nonenol (10% in propylene-glycol) | 40 |
| Lilial ® Givaudan (p-tert.butyl-α-methylhydrocinnamaldehyde (10% in propyleneglycol) | 20 |
| Lemon oil | 20 |
| Propyleneglycol | 200 |
| | 800 |

If there are added to this melon base 180 parts of I, then there is obtained a novel base having a much more succulent melon character. The novel base is more natural, fresher and stronger. The impression of a sugar melon predominates, while the original base is more reminiscent of water melon.

EXAMPLE 8

| Apple flavour | Parts by weight |
|---|---|
| Maltol | 0.2 |
| Benzaldehyde | 0.3 |
| Citral | 0.3 |
| Vanillin | 0.3 |
| d-Limonene | 0.5 |
| Cis-3-hexenyl acetate | 0.5 |
| γ-Undelactone | 0.5 |
| Capronaldehyde | 1.5 |
| Ethyl butyrate | 4.0 |
| n-Hexanol | 18.0 |
| n-Hexyl acetate | 50.0 |
| Ethanol | 901.9 |
| | 980.0 |

If there are added to this apple flavour 20 parts of a 10% solution of I in ethanol, then the previously pronounced ester-like note is reduced. In place of this note a pleasant fruity note now appears. Regarding flavour, a considerable improvement is ascertainable using 100 g of the novel apple flavour per 100 liters of sugar syrup, diluted with water 1:5. In complete contrast to the original flavour (a conventional, fantasy-free apple flavour) the pleasant, sweet, fruity flavour note is now reminiscent of the "Golden Delicious" apple.

EXAMPLE 9

| Pear flavour | Parts by weight |
|---|---|
| Anethol (10% in ethanol) | 0.2 |
| Linalyl acetate (10% in ethanol) | 0.2 |
| Vanillin (10% in ethanol) | 1.0 |
| Hexyl acetate | 4.0 |
| Ethyl 2,4-decadienoate | 5.0 |
| Ethyl acetate | 5.0 |
| Piperonyl acetate | 10.0 |
| Geranyl propionate | 15.0 |
| Isoamyl acetate | 50.0 |
| Ethanol | 889.6 |
| | 980.0 |

If there are added to this pear flavour 20 parts of a 10% solution of I in ethanol, then the former obtrusive ester-like note is suppressed in favour of a pleasant, sweeter and more fruity note. Regarding flavour, a significant improvement is ascertainable using 100 g of the novel pear flavour per 100 liters of sugar syrup, diluted with water 1:5. In contrast to the original, conventional flavour, the character of table pears now comes into play.

We claim:
1. Compounds of the formula

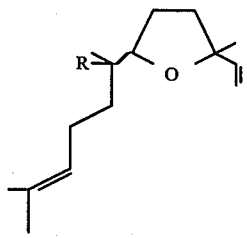

wherein R represents a hydroxy or acyloxy group.
2. Compounds in accordance with claim 1, having the formula:
2-methyl-2-vinyl-5-(1'-hydroxy-1',5'-dimethyl-hex-4'-en-1'-yl)-tetrahydrofuran.
3. Compounds in accordance with claim 1, having the formula:
2-methyl-2-vinyl-5-(1'-acetoxy-1',5'-dimethyl-hex-4'-en-1'-yl)-tetrahydrofuran.

* * * * *